(12) United States Patent
Lefkus, III et al.

(10) Patent No.: US 9,027,297 B2
(45) Date of Patent: May 12, 2015

(54) RELOCATABLE RADIATION VAULT AND METHODS OF ASSEMBLY AND USE

(75) Inventors: John J. Lefkus, III, Annandale, NJ (US); Eric Landau, Clearwater, FL (US); Cheri A. Oquist, Pembroke Pines, FL (US)

(73) Assignee: RAD Technology Medical Systems LLC, Aventura, FL (US)

( * ) Notice: Subject to any disclaimer, the term of this patent is extended or adjusted under 35 U.S.C. 154(b) by 0 days.

(21) Appl. No.: 13/459,694

(22) Filed: Apr. 30, 2012

(65) Prior Publication Data

US 2013/0111825 A1 May 9, 2013

Related U.S. Application Data

(63) Continuation of application No. PCT/US2010/054601, filed on Oct. 29, 2010.

(60) Provisional application No. 61/256,984, filed on Oct. 31, 2009.

(51) Int. Cl.
| | |
|---|---|
| *E04H 3/08* | (2006.01) |
| *A61N 5/10* | (2006.01) |
| *E04H 1/12* | (2006.01) |
| *G21F 3/00* | (2006.01) |

(Continued)

(52) U.S. Cl.
CPC .. *E04H 3/08* (2013.01); *A61N 5/10* (2013.01); *E04H 1/1205* (2013.01); *G21F 3/00* (2013.01); *G21F 7/00* (2013.01); *E02D 31/008* (2013.01)

(58) Field of Classification Search
CPC ......... E04H 1/02; E04H 1/1205; E04H 1/125; E04H 1/1277; E04H 2001/1283; E04H 3/00; E04H 3/08; E04H 7/00; E04H 7/28; E04H 9/00; A61G 3/001; A61G 10/00; A61G 2210/50
USPC .......... 52/64, 239, 79.1, 79.5, 292; 296/24.38
See application file for complete search history.

(56) References Cited

U.S. PATENT DOCUMENTS

| | | | |
|---|---|---|---|
| 4,785,593 A | 11/1988 | Munoz, Jr. | |
| 5,695,443 A * | 12/1997 | Brent et al. | 588/249 |

(Continued)

FOREIGN PATENT DOCUMENTS

| | | |
|---|---|---|
| DE | 10234357 A1 | 7/2013 |
| EP | 1430932 B1 | 2/2008 |

(Continued)

OTHER PUBLICATIONS

International Search Report and Written Opinion, PCT/US2010/054601, Rad Technology Medical System, LLC et al., Jul. 22, 2011.

(Continued)

*Primary Examiner* — Jessica Laux
(74) *Attorney, Agent, or Firm* — John M. Bradshaw; Overhauser Law Offices LLC

(57) ABSTRACT

A temporary radiotherapy facility for use during renovation, upgrading, and/or modernization of an existing facility. The radiotherapy facility is integrated with radiation producing equipment and radiation shielding vaults. The structural elements and their arrangement enable compliance with applicable codes for this type of facility and provide an ability to maintain radiotherapy treatment continuity during equipment transition.

12 Claims, 8 Drawing Sheets

(51) Int. Cl.
*G21F 7/00* (2006.01)
*E02D 31/00* (2006.01)

(56) References Cited

U.S. PATENT DOCUMENTS

| | | | |
|---|---|---|---|
| 6,973,758 | B2 | 12/2005 | Zeik et al. |
| 7,665,249 | B2 | 2/2010 | Zeik et al. |
| 8,151,537 | B2 * | 4/2012 | Pope .................. 52/745.02 |
| 2004/0025448 | A1 | 2/2004 | Puusepp et al. |
| 2007/0269008 | A1 | 11/2007 | Pomper |

FOREIGN PATENT DOCUMENTS

| | | | |
|---|---|---|---|
| JP | 5851115 | B2 | 11/1983 |
| JP | 5940992 | B2 | 10/1984 |
| JP | 06-264623 | A | 9/1994 |
| JP | 09-291545 | A | 11/1997 |
| JP | 2003-221974 | | 8/2003 |
| JP | 2009-228349 | | 10/2009 |
| WO | WO2008-100827 | A1 | 8/2008 |

OTHER PUBLICATIONS

R. Prabhakar M.SC., et al., Quantification of Shift in Isocenter for 2-Dimensional and 3-Dimensional Radiotherapy Plans for Various Common Treatment Sites, Feb. 13, 2009, http://www.ispub.com/journal/the-internet-journal-of-oncology/volume-4-number-1/quantification-of-shift-in-isocenter-for-2-dimensional-and-3-dimensional-radiotherapy-plans-for-various-common-treatment-sites.html.

Supplemental EP Search Report—EP 10 82 7506—May 23, 2014.

* cited by examiner

RELOCATABLE RADIATION VAULT AND METHODS OF ASSEMBLY AND USE

CROSS-REFERENCE TO RELATED APPLICATIONS

This application is a continuation of PCT/US2010/054601 filed Oct. 29, 2010, which claims the benefit of U.S. Provisional Application No. 61/256,984, filed Oct. 31, 2009, the disclosures of which are incorporated by reference.

BACKGROUND OF THE INVENTION

The present invention relates to a complete radiation therapy facility, including a therapeutic radiation producing (or emitting) device and the shielding structures necessary to safely produce the therapeutic radiation and methods for making and using the same. More particularly, but not exclusively, the present invention relates to a radiotherapy vault and integrated clinical functions suitable for use on a temporary basis, such as during the time an existing facility is undergoing an equipment upgrade or facility renovation. The various structural features which are illustrated and described herein result, collectively, in a fully equipped and integrated radiotherapy clinical facility. A further structural feature of the disclosed integrated solution is the overall size compactness given the performance demands and requirements.

Radiation emitting equipment has a number of well known applications. Radiation emitting equipment is used to inspect packages and cargo at borders and to perform non-destructive testing. In the medical field, radiation emitting equipment is used in the diagnosis and treatment of a number of diseases. Not surprisingly, the manufacturers of this equipment are continually making improvements. Radiation emitted by equipment of the type described as "therapeutic" or "for treatment" is often referred to as "high energy", and is typically greater than 1 mv.

For example, radiation therapy (a.k.a. radiotherapy) has become widely used in the treatment of cancer and several other non-malignant conditions, and modern radiotherapy equipment has improved abilities to target and destroy specific tissues while sparing surrounding healthy tissue. As a result, the use of up-to-date radiotherapy equipment can yield improved patient outcomes as well as provide other benefits to the operators of the facility, such as increased ease of use, increased efficiency, and/or increased patient throughput.

Despite these benefits, it has not been practical for many existing radiotherapy facilities to modernize. Existing radiotherapy equipment, like many other types of radiation emitting equipment, is typically housed within a radiation shielding vault so as to protect the surrounding personnel from the harmful effects of the radiation. Because of the high radiation levels involved (i.e. typically greater than 1 MV) existing vaults are often constructed underground and/or with concrete walls that are several feet thick. As a result, the process of removing existing equipment, installing a modern replacement unit, and performing any necessary remodeling and reconfiguration is typically a three to five month process, with some projects taking up to a year. The prospect of a radiotherapy facility being out of service for such an extended duration, with the resultant disruption of treatment to patients, loss of revenue to the facility, and potential loss of referrals, is simply unacceptable to many facility operators. As a result, it is estimated that there are thousands of medical linear accelerators in use today which are technically obsolete and in need of immediate replacement.

In one form, the present invention addresses this need.

BRIEF SUMMARY

The present invention provides systems and techniques for constructing and using integrated radiotherapy treatment facilities which include radiation producing equipment and radiation shielding vaults. While the actual nature of the invention covered herein can only be determined with reference to the claims appended hereto, certain aspects of the invention that are characteristic of the embodiments disclosed herein are described briefly as follows.

According to one aspect, the present invention provides a temporary, building code compliant radiotherapy facility for use during the time when an existing facility is being upgraded or modernized.

According to another aspect, the present invention provides a method of maintaining radiotherapy treatment continuity during an equipment transition.

According to another aspect, the present invention provides a building code compliant temporary radiotherapy facility which can be erected and put into use rapidly and cost effectively.

According to another aspect, the present invention provides a new method of constructing a foundation for radiation shielding vaults.

According to another aspect, the present invention provides a new method of coupling a radiation shielding vault to a foundation.

According to another aspect, the present invention provides a new approach for supporting radiation shielding material over a treatment area and distributing the load of that radiation shielding material to a supporting foundation.

According to another aspect, the present invention provides for the construction of a radiotherapy facility wherein the foundation which supports the treatment room is decoupled from the foundation which supports the mass of radiation shielding material above the treatment room.

According to another aspect, the present invention provides a new design for providing a roof over a radiation treatment vault.

According to another aspect, the present invention provides a new mechanism for installing the shielding door for a vault.

According to another aspect, the present invention integrates required clinical, radiotherapy room and accelerator equipment with required electrical and mechanical support systems in a singular compact and complete solution.

These and other aspects are discussed below.

BRIEF DESCRIPTION OF THE SEVERAL VIEWS OF THE DRAWINGS

Although the characteristic features of this invention will be particularly pointed out in the claims, the invention itself, and the manner in which it may be made and used, may be better understood by referring to the following description taken in connection with the accompanying figures forming a part thereof.

DETAILED DESCRIPTION

Figure 1:
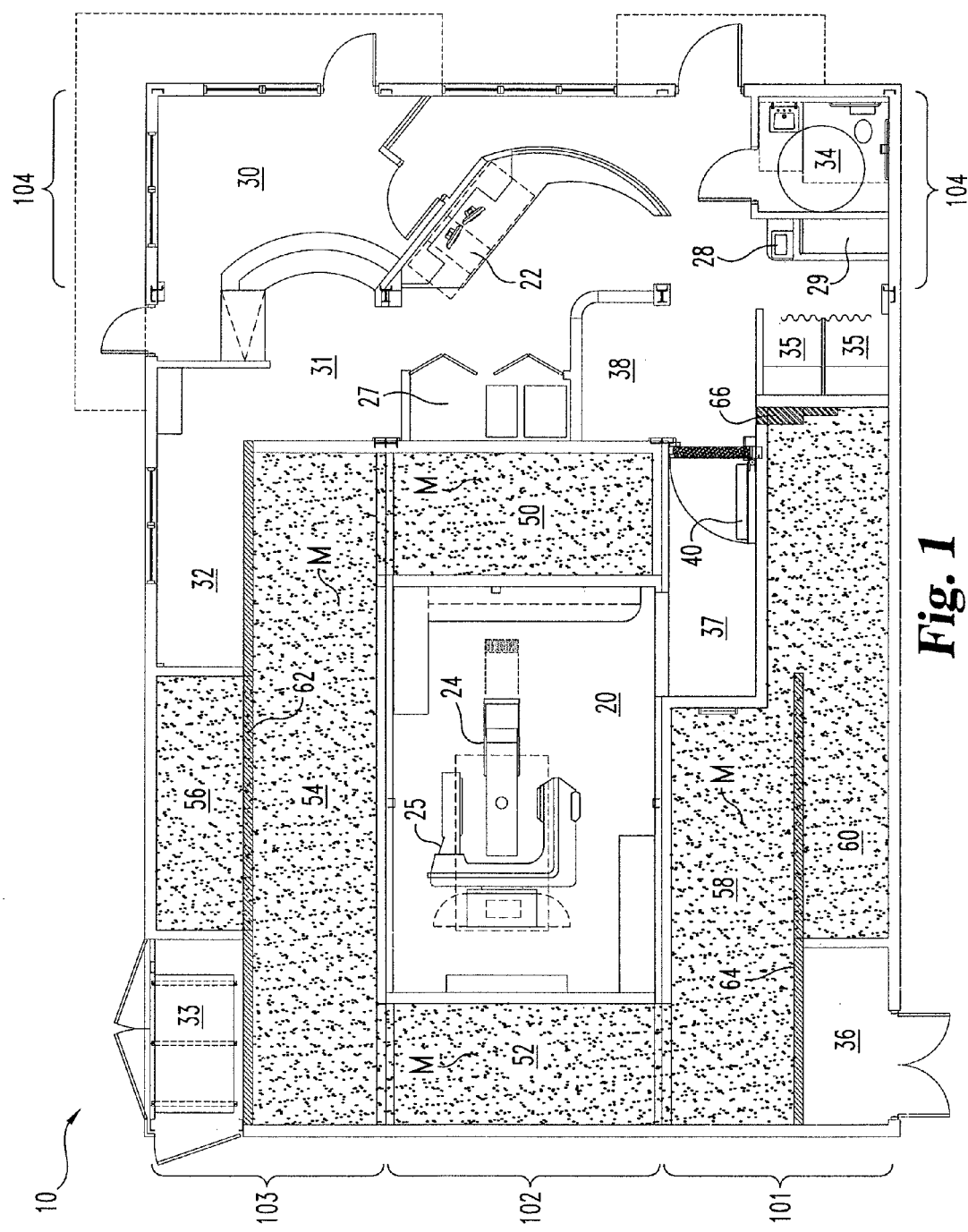
FIG. 1 shows the floor plan of a completed radiotherapy facility according to one embodiment.

For the purposes of promoting an understanding of the principles of the invention, reference will now be made to the embodiments illustrated in the drawings and specific language will be used to describe the same. It will nevertheless be understood that no limitation of the scope of the invention is hereby intended. Alterations and further modifications in the illustrated devices, and such further applications of the principles of the invention as illustrated herein are contemplated as would normally occur to one skilled in the art to which the invention relates.

General Overview

In one form, the present invention involves the provision of a fully functioning temporary radiotherapy facility intended for short term use. The temporary facility may be provided at a designated site and used to treat patients during the time when an existing radiotherapy facility is being upgraded or modernized. Upon completion of the upgrade, the temporary facility may be removed from the site and redeployed to another site in need of a similar service.

Figure 2:
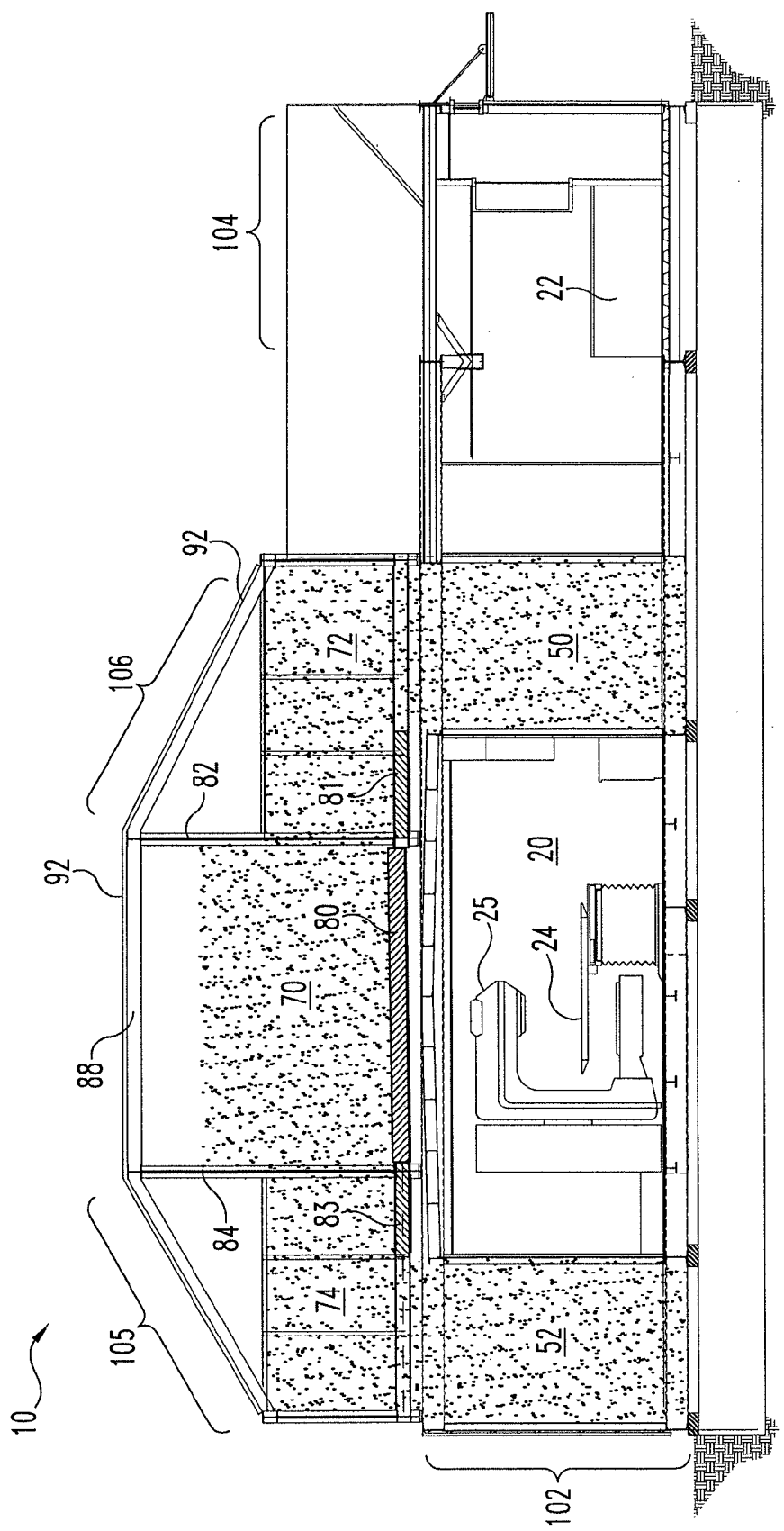
FIG. 2 is a side elevational view, in full section, of the FIG. 1 facility.
Figure 3:
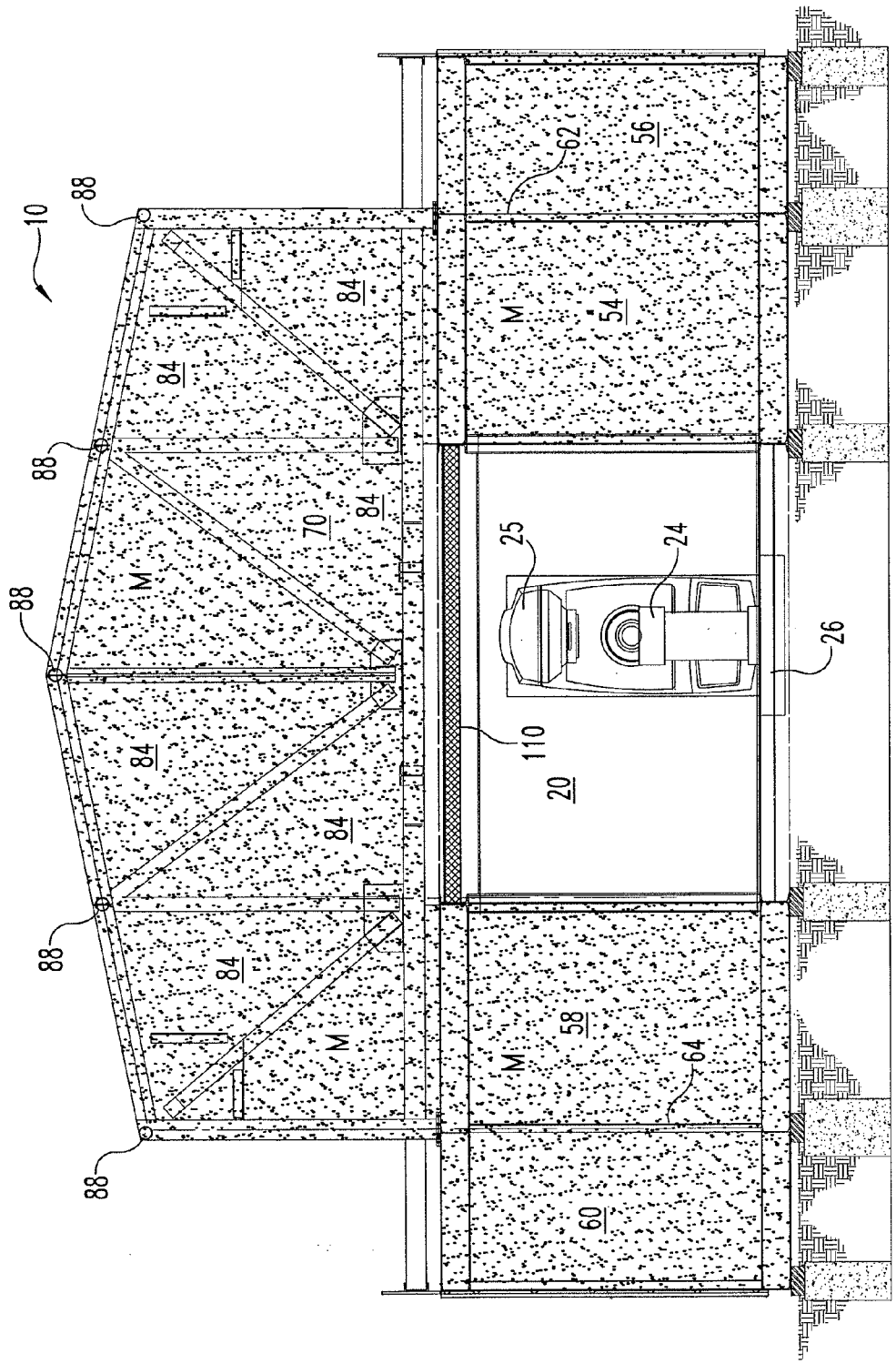
FIG. 3 is an end elevational view, in full section, of the FIG. 1 facility.

Referring to FIGS. 1-3, temporary radiotherapy facility 10 includes a treatment room 20 including a radiotherapy device 25 and a control station 22 for the radiotherapy device 25. The interior of facility 10 includes waiting area 30, reception/scheduling area 31, gowning area 35, restroom 34, and storage areas 32, 38. The mechanical area 33 contains any necessary heating and chiller equipment and is accessed externally, as is an additional storage area 36. The facility further includes an electrical closet 27, staff sink 28 and a potable and waste water tanks 29.

Access to treatment room 20 is via a radiation shielded door 40 and corridor 37. Once inside the treatment room 20, the patient lies on the treatment table 24 and the radiotherapy is administered via radiotherapy device 25 in accordance with the treatment parameters input by the operator at the control station 22.

When fully constructed, the facility 10 complies with applicable building codes. Further, the facility 10 is "habitable" in the context of supporting patients and medical personnel during the time of use. As used herein, "code compliant" and "building codes" are intended to encompass an ability to construct and configure the basic structural elements of the disclosed combination so as to meet or adhere to what would be required according to applicable building codes. Since the codes of local municipalities might change over time, the structural embodiment disclosed herein is geared toward the code requirements as currently set forth in the 2009 Edition of the ICC International Building Code® (ISBN: 1580017258), including those other codes referenced therein.

TRV Design

Facility 10 has been designed using a number of prefabricated modules so as to speed the process of assembling and disassembling the structure, and may be referred to as a Temporary Radiotherapy Vault (TRV). As shown in FIG. 1, the ground floor is composed of four different modules, each of which has a generally rectangular footprint. Modules 101, 102 and 103 are equal in length and are placed along side each other and module 104 is placed across the ends of modules 101, 102, and 103 (right side of FIG. 1). Alternative configurations or embodiments could incorporate more than four different modules.

In this illustrated configuration, the treatment room is entirely contained within module 102. Modules 101, 102 and 103 are designed such that, when assembled, they define a number of void spaces 50, 52, 54, 56, 58, and 60 around the treatment room 20. These void spaces (i.e., the vessel) are designed to be filled with a radiation shielding material M, such as a flowable granular fill having a density range of 80-125 lb/ft$^3$. Aligned void spaces (e.g. 50 and 54, 54 and 52, 52 and 58) are in fluid communication such that, once filled with the shielding material, a substantially continuous barrier of the radiation shielding material is created around the treatment room 20. By remaining in a perpetually flowable state, the granular fill (i.e., the shielding material M), cannot crack due to settling or seismic events.

Roof modules 105 and 106 are designed so as to be placed above modules 101, 102 and 103 and to have their trusses 84 and 82 spanning from the shear wall 64 in module 101 to the shear wall 62 in module 103. A supporting panel 80 is then mounted between the trusses 84 and 82, and together with panels 81, 83 integrated into the roof modules 106, 105 supports the shielding material M over the treatment room 20 while maintaining a gap 110 between the underside of the panels 80, 81, 83 and the uppermost portion of the treatment room 20. Alternative configurations and embodiments could incorporate additional roof modules in lieu of supporting panels. As a result, the load of the shielding material directly above the treatment room 20 can be distributed through the trusses to the shear walls 62, 64 rather than bearing on the treatment room itself. This gap isolates the treatment room and protects it from the effects of any foundation shifting or sinking that may occur due to the excessive weight of the shielding material above it. As shown in FIGS. 2 and 3, the upper level shielding areas 70, 72 and 74 that are not directly above the treatment room 20 are open to the lower level void spaces 50, 52, 54, 58. Connecting rods 88 span between the upper portions of the trusses 84, 82 and help give shape and support to fabric or membrane roof 92 which is installed once all the shielding material has been delivered.

While some of the floor space for control station 22 is provided by module 104, it is preferable to have the relevant computer equipment hardwired to the radiotherapy device 25 in module 102. In this case, the computer equipment is provided on a wheeled cart so that it can move into the position shown in FIG. 1 from a storage position in module 102.

Radiation Shielding

The precise quantity and desired distribution of radiation shielding material is dependent on the characteristics of the radiation emitted from device 25. As illustrated, the facility 10 is configured to employ an isocentrically arranged high energy linear accelerator, which typically operates in the range of 4-25 MV. An example would be Varian Medical Systems Trilogy, Palo Alto, Calif. In order to provide the appropriate level of shielding, the total weight of the shielding material may be 1,000,000 lbs or 2,000,000 lbs or more. To the extent the linear accelerator is operated at high MV energies (i.e. above 10 MV), neutron shielding is provided by lining the treatment room with wood panels and borated polyethylene sheets.

The facility 10 could also be used to perform other types of radiotherapy, such as gamma knife or high dose rate brachytherapy (HDR), which typically operate in the range of 1-3 MV. The facility 10 may also be adapted for use with cyclotrons operating in the range of 10-15 MV or proton accelerators operating in the range of 40-250 MV.

Foundation

Existing Rad Pro Foundations

Figure 8:
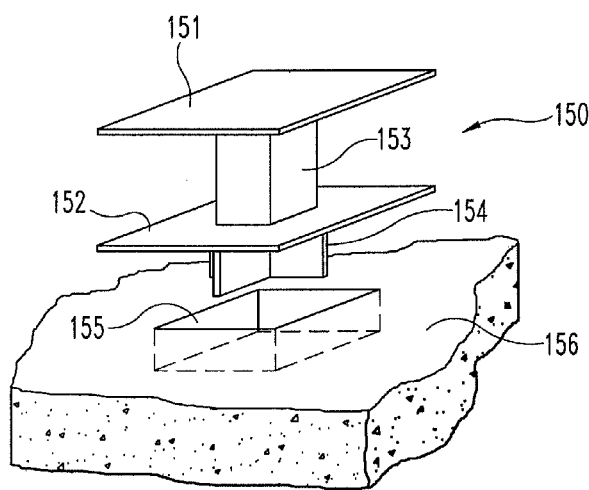
FIG. 8 is a diagrammatic perspective view showing the installation of supports in a concrete slab as per existing installations of the system corresponding to U.S. Pat. No. 6,973,758 (the Rad Pro).

Existing modular vaults corresponding to U.S. Pat. No. 6,973,758 (i.e. the Rad Pro System) have been constructed on a reinforced concrete slab foundation in a number of permanent installations. The base of the Pro System pods was typically elevated several inches above the slab by a series of stub columns 150 as shown in FIG. 8. These stub columns 150 were fabricated from high strength steel and included a hollow vertical supporting column 153 with horizontal plates 151, 152 at each end. The vertical column 153 was in the shape of a rectangular solid with a square horizontal cross section. Shear lugs 154 were welded to the underside of the bottom plate in the form of a pair of vertical extension plates intersecting at right angles so as to generally form a "+". In use, a square cross section recess 155 was first provided in the concrete slab 156. The recess 155 was then filled with grout (not shown) and the shear lugs 154 were set into the grout filled recesses.

New Foundation for TRV

With reference to FIGS. 4-7, the foundation 200 for the TRV (facility 10) comprises a pattern (FIG. 4) of elongated beams of reinforced concrete. Individual beams of reinforced concrete are conventionally referred to as grade beams, since they are typically constructed at or above grade level. The grade beams for the TRV foundation are recessed several inches below-grade (e.g. 3-6 inches). The use of below-grade, grade beams makes it easier to return the site to its original condition once the TRV has been removed, since one could simply backfill over the below-grade, grade beams.

The pattern includes a number of parallel and orthogonal beams and beam segments. These beams underlie various portions of the TRV structure and the layout of FIG. 4 corresponds to the floor plan of FIG. 1. Of note, parallel beams 210 and 212 underlie the elongated sides of module 102 and short transverse beams 214, 215 and 216 span between beams 210 and 212 at multiple locations along the lengths of beams 210 and 212. These short transverse beams 214, 215, 216 serve to provide a degree of integration or coupling between beams 210 and 212, and they also serve to underlie and provide support for the base frame 26 in module 102 to which the radiotherapy device 25 is mounted. On the other hand, beams 214, 215, 216 do not intersect with the outside beams 220 or 230, and thus these outside beams are relatively decoupled from their respective inner beam 212, 210. In other words, the presence of beams 214, 215, 216 assures that beam 210 is more coupled to beam 212 than it is to beam 230.

This is significant because beams 220 and 230 are designed to underlie and provide support to the shear walls 62 and 64 in modules 103 and 101 respectively. As explained previously, because of the relationship between platforms 80, 81, 83 and trusses 82, 84, these shear walls 62, 64 bear the load of all the suspended shielding material that is positioned over the treatment room 20. Because this is a large mass of material, it provides significant inertial resistance to any lateral movement that would develop during a seismic event (i.e. earthquake). As a result, in order to satisfy various building codes, it is generally necessary to have a lateral coupling between the foundation and the shear wall that can withstand the significant lateral stresses. The dead load of the suspended shielding material is also positioned far enough away from the therapy room 20, to avoid any impairment to the supporting beams 214, 215, 216 which may impact the rooms geometry and level.

Keyways

Figure 4:
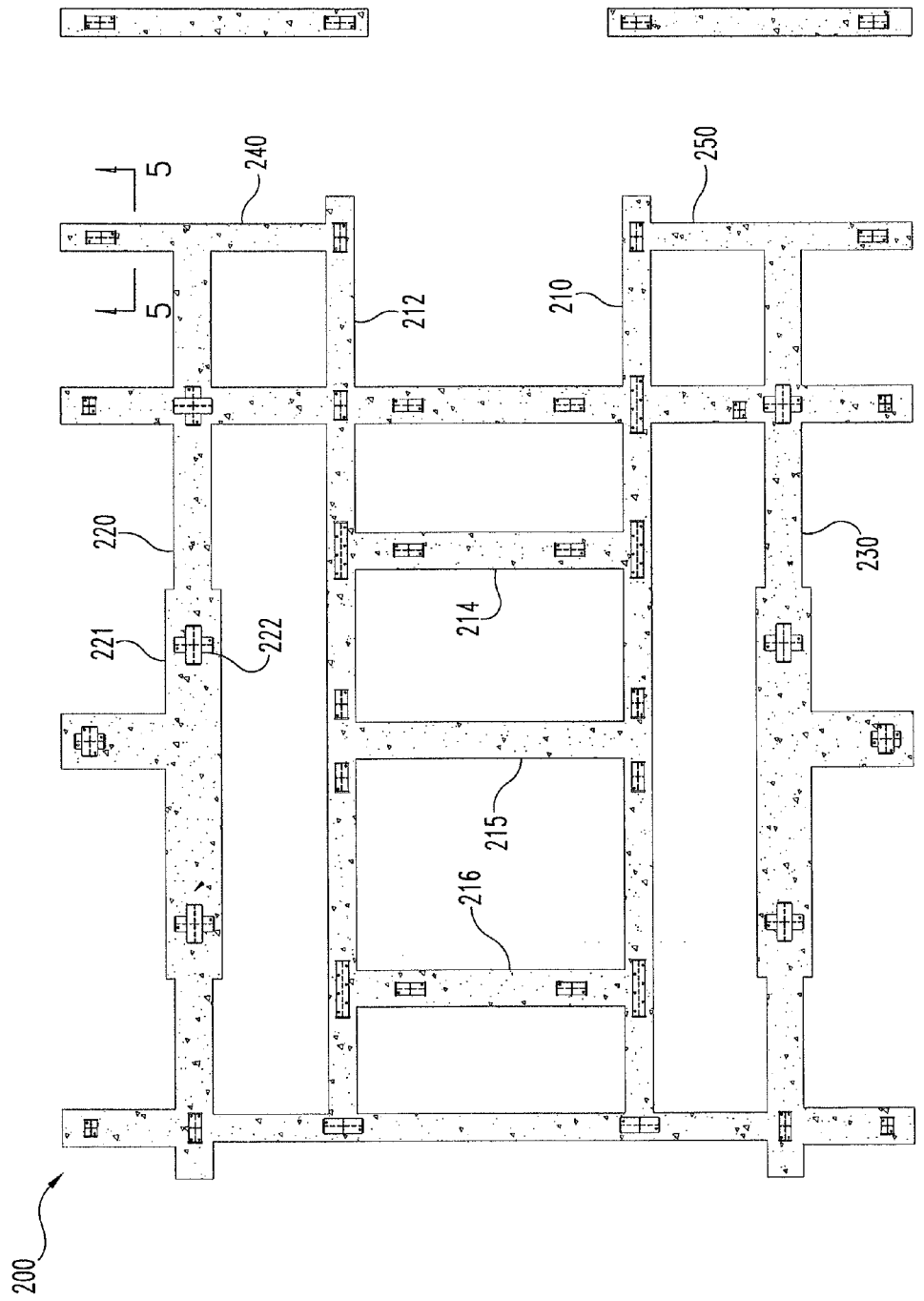
FIG. 4 is a top plan view layout of the foundation for the FIG. 1 facility.
Figure 5:
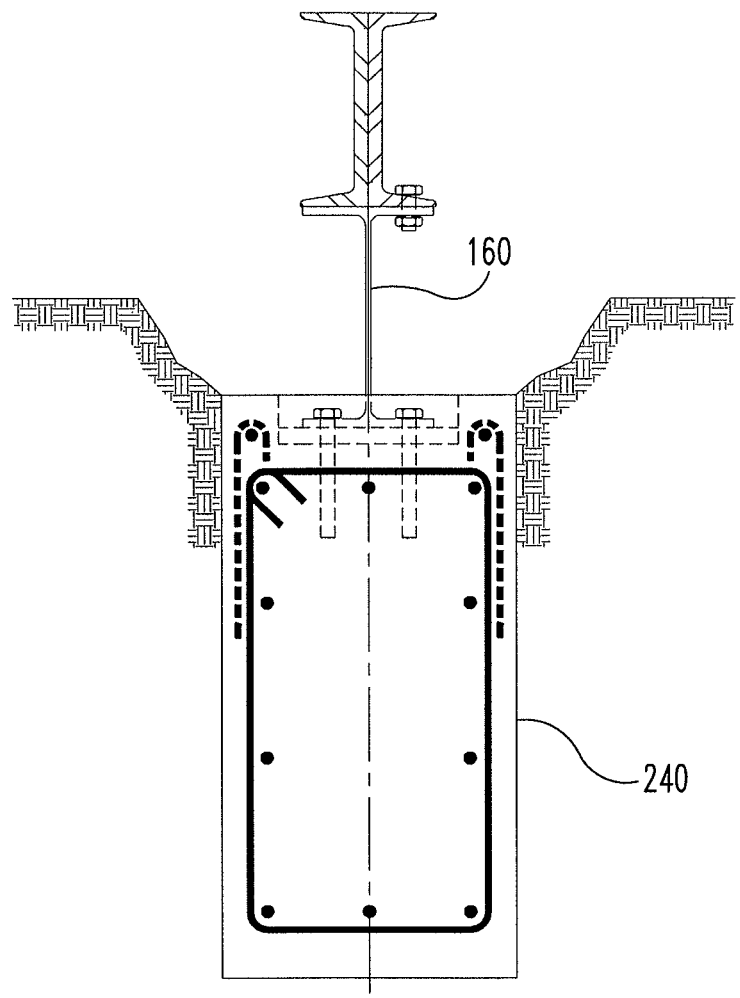
FIG. 5 is a partial, end sectional view of the foundation as viewed along line 5-5 in FIG. 4.
Figure 6:
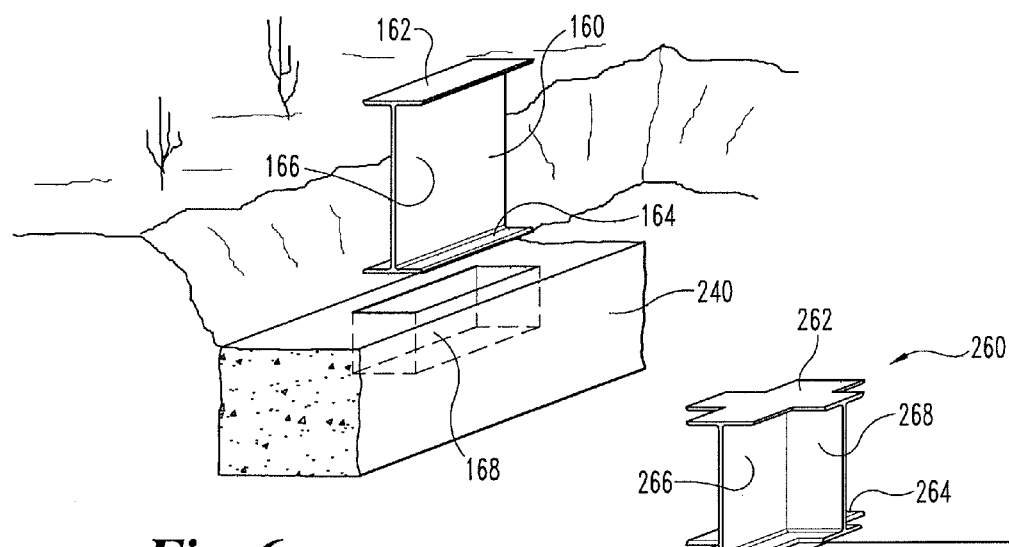
FIG. 6 is a diagrammatic perspective view showing the installation of a support in a foundation beam.
Figure 7:
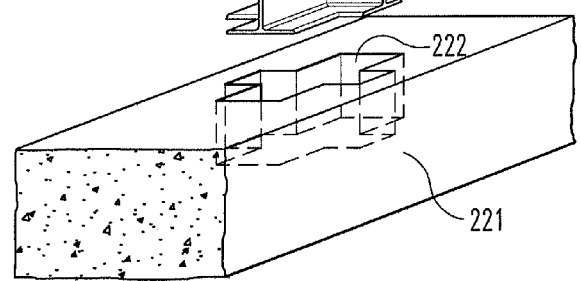
FIG. 7 is a diagrammatic perspective view showing the installation of another support in a foundation beam.

With reference to FIGS. 6 and 7, coupling between the TRV modules and the foundation grade beams is provided by one of two types of supports. Supports 160 are generally in the form of an I beam and have a planar base 164 and top plate 162 coupled by a vertical section 166. Support 160 is designed to be mounted in an elongated horizontal slot 168 such as the one formed in grade beam 240. Grade beams 240 and 250 are illustrated in FIG. 4. By virtue of the planar base 164 of support 160 being recessed into slot 168, the sidewalls of slot 168 provide lateral coupling through contact with the sides of base 164 and vertical span 166. If the slot 168 is initially too long to provide adequate lateral coupling contact, such contact can be facilitated by providing grout into the ends of slot 168.

While illustrated as having only a single vertical span 166, support 160 may be reconfigured so as to include additional or different vertical spans between top plate 162 and base 168. For example, vertical plates may be added to the ends of the support 160 so as to provide additional coupling between the top plate 162 and the base 168. These end plates would be orthogonal to the vertical span 166 and would increase the overall rigidity of the supports 160.

Supports 260 are similar to supports 160 in that they also have a planar mounting plate 262 and a planar base 264 and the planar base 264 is received in slot 222 of a grade beam 221. However, the slot 222 includes a pair of intersecting slots such that slot 222 is considered to be elongated in two orthogonal directions. The base 264 of support 260 is also of a "+" or intersecting configuration, and in use the base of support 260 is received in slot 222 and engages therewith so as to provide lateral contact coupling in multiple directions.

Supports 260 may also be supplemented with additional vertical plates. In particular, it is contemplated that four vertical end plates would be attached to the four ends of support 260. Two opposing plates would be attached orthogonal to vertical support 266 and two would be orthogonal to vertical support 268.

Door Cassette

Figure 9:
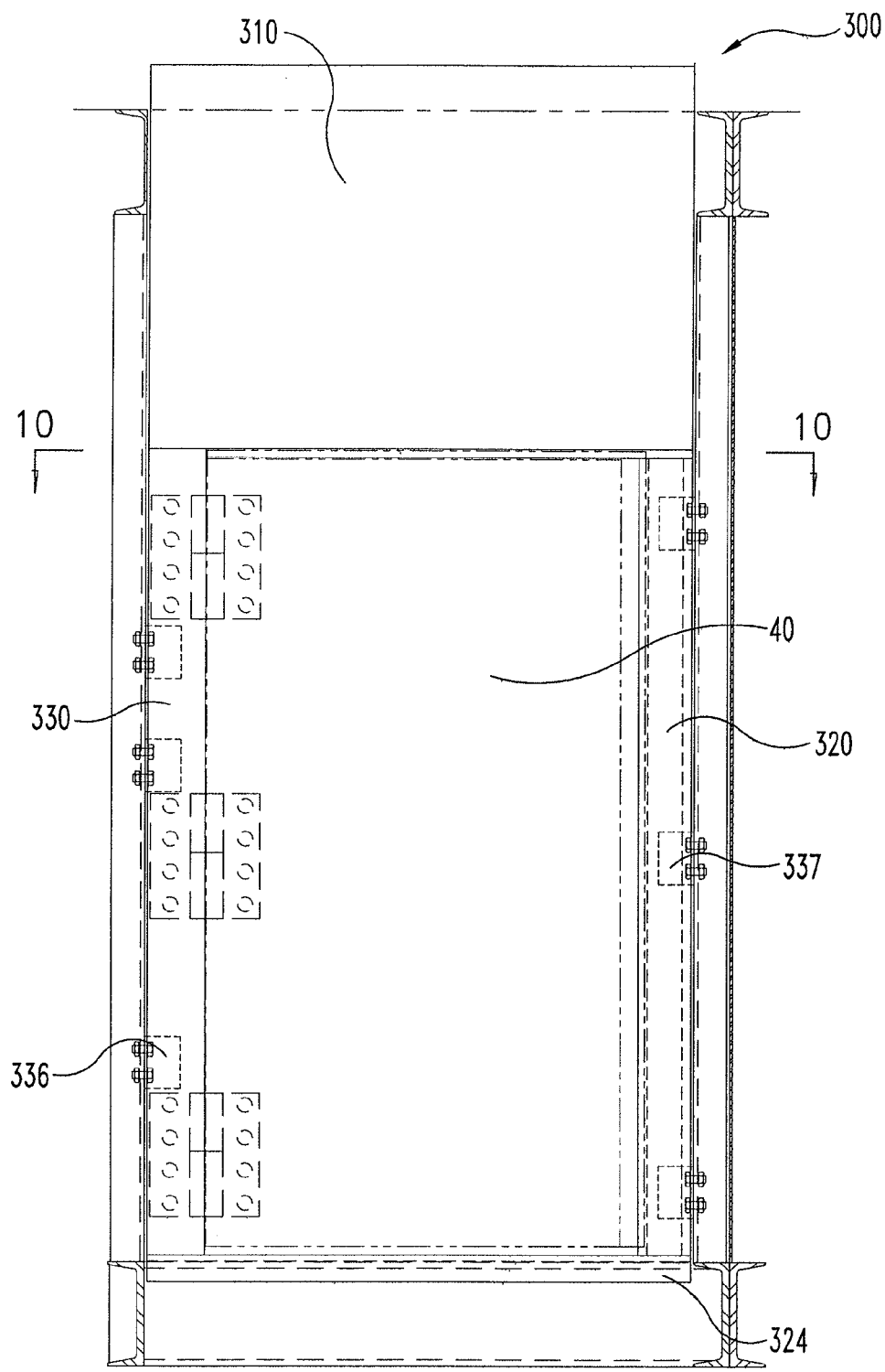
FIG. 9 is an elevational view showing the radiation shielding door cassette installed in the facility of FIG. 1.
Figure 10:
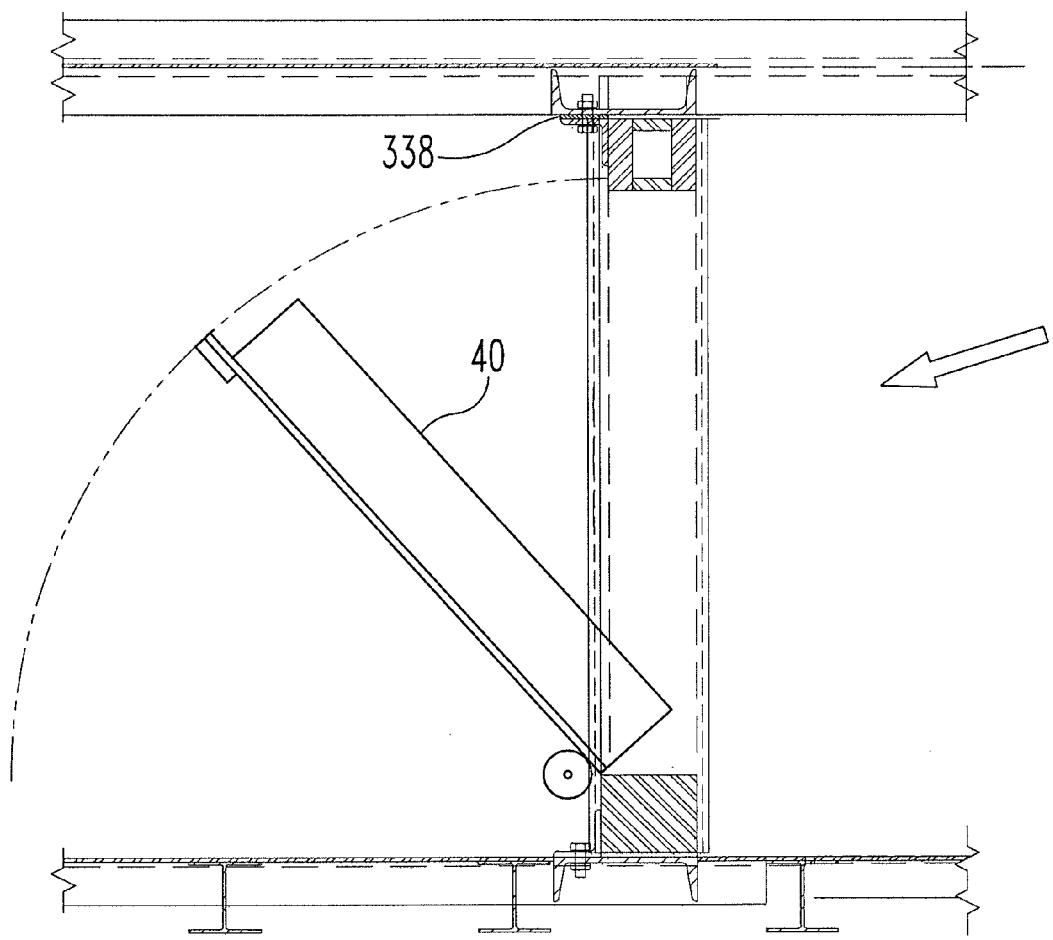
FIG. 10 is a partial, top view, as viewed along line 10-10 in FIG. 9.

FIGS. 9 and 10 illustrate the door cassette 300 installed in module 101. Door cassette 300 includes a shielding door 40, its surrounding frame parts 320, 330, 324, and a radiation shielding transom area 310 directly above the door 40. The entire cassette 300 is configured to be lifted out of module 101 as a whole. When inserted into position, the lower portion of frame 324 (i.e. the threshold) is recessed into a corresponding opening in the floor of module 101 (not shown). The hinge side of frame 330 abuts against channel steel in the module 101 and is bolted in place via clamps 336. The opposing door side of frame 320 has a clearance that is filled with shim plate 338 and then the door side of frame 320 is bolted to module 101 via clamps 337. With reference to FIG. 1, additional shielding plates 66 are provided in module 101 to provide shielding otherwise lost due to corridor 37, which cannot being filled with granular fill shielding material M.

Methods of Use

One contemplated method according to the present invention involves the identification of a radiotherapy facility having an existing radiotherapy device needing to be taken out of service. Typically, a facility would self identify its needs.

Next, a site for a temporary radiotherapy facility is identified. The site should be suitably close to the existing facility so as to minimize disruption, and may be an empty field or parking lot. A foundation for the temporary device is created at the identified site. The foundation can be a simple concrete slab, but preferably it is a pattern of recessed grade beams as described previously.

Next, a temporary radiotherapy facility is assembled on the foundation. The temporary radiotherapy facility typically includes a radiotherapy device within a radiation shielding vault, and it may correspond to the TRV previously described. The vault may include at least about 1,000,000 lbs of radiation shielding material, such as the granular fill or some other type, as previously described, including water.

When the need for the radiotherapy facility ceases to exist, for example because the renovation has been completed, the facility is removed. For a typical replacement, this would be less than 12 months. Removal of the temporary facility may include removal of some or all of the components of the TRV and some or all of the radiation shielding material included in the void spaces.

In one refinement, the TRV is equipped with radiotherapy equipment substantially similar to the equipment to be installed at the existing facility. In this way, the personnel can receive training on the new equipment while operating in the TRV.

Another inventive method contemplated herein involves maintaining treatment continuity to a patient population during the renovation or construction of a radiotherapy facility. This may be accomplished in connection with an existing (first) radiotherapy facility having a first radiotherapy device, wherein services are provided at the existing facility to a patient population by support staff, the support staff including at least one treatment individual. The treatment individual may be, for example, a doctor, a nurse, a therapist, a dosimetrist, or a physicist.

A second radiotherapy facility is constructed to treat the patient population on a temporary basis, the second facility having a second radiotherapy device within a radiation shielding vault, such as the TRV described previously. Upon completion of the temporary facility, the treatment individual is transitioned to the second facility, and he/she provides services at the second facility to the patient population during the renovation and/or upgrade of the first radiotherapy facility. Then, upon completion of the renovation and/or upgrade of the first radiotherapy facility, the treatment individual is transitioned back to the first facility (or to a newly-constructed third facility) where he/she can continue to serve the same patient population. The period of transition may be occasioned by an equipment modernization and/or the construction of a wholly-new facility.

Maintaining Isocenter for Radiotherapy Equipment

In order to be effectively used, radiotherapy equipment must be carefully calibrated. One of the alignment and/or calibration characteristics is referred to as "isocenter" which is a point in three-dimensional space around which all movable axes of the treatment machine revolve. As would be understood, a stable isocenter is critical. In certain applications, isocenter is defined and specified as a sphere having a radius of no more than 0.5 mm in diameter. The targeted treatment area, usually a tumor, is placed at isocenter during treatment. As various components of the treatment machine (gantry, collimator, and couch) are moved to different angles during the treatment delivery, it is essential that no part of the machine flex or move in any manner that would cause the target, at isocenter, to be missed.

All structures can sink, shift, or even move. They are engineered to do this without any overall impairment to the structure. A shift in a wall, floor or ceiling in a therapy room, however, has consequences not normally part of the engineer's design challenge. With a slab foundation, soil settlement is controlled since the slab can bridge over settlement areas, just like a sheet of plywood would bridge your shoe depressions in the mud. If there is any settlement, it will be mitigated by the slab, or at least slowed down so as to happen over a longer period of time, typically years.

Rapid settlement in localized areas can have an effect on grade beams, since they do not have the benefit of the monolithic slab. The disclosed approach, as set forth herein, is to build in tolerance by making the therapy room an independent structural sanctuary that is not impacted by any settlement caused by the huge shielding mass, especially the mass directly above the treatment room. This is achieved by creating a six inch gap between the therapy room structure and the supported shielding mass above. Further contributing to this achievement is allowing the grade beams to move independently and further, separating the shielding mass load from the therapy room load by a suitable distance on independent grade beams.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Thus, the specifics of this description and the attached drawings should not be interpreted to limit the scope of this invention to the specifics thereof. Rather, the scope of this invention should be evaluated with reference to the claims appended hereto.

In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" is used in connection with a device or system component, such as a fluid processing unit or electrical device, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A method for providing radiotherapy while an existing radiotherapy device is taken out of service, the method comprising:

providing a radiotherapy facility having an existing radiotherapy device needing to be taken out of service;

providing a site for a temporary radiotherapy facility to be used while the existing radiotherapy device is taken out of service;

providing a foundation for the temporary radiotherapy facility at the site;

constructing a temporary radiotherapy facility on the foundation, the temporary radiotherapy facility including a radiotherapy device within a radiation shielding vault, the radiation shielding vault including at least about 1,000,000 lbs of radiation shielding material; and removing the temporary radiotherapy facility from the site less than 12 months from the time the existing equipment is taken out of service, wherein removing the temporary radiotherapy facility includes removing the radiotherapy device and the radiation shielding vault from the site.

2. The method of claim 1 wherein the radiotherapy device within the temporary facility comprises a high energy radiotherapy device.

3. The method of claim 1 wherein removing the facility includes removing at least about 1,000,000 lbs of radiation shielding material.

4. The method of claim 1 wherein the site comprises land which is owned or leased by the operator of the radiotherapy facility.

5. The method of claim 1 wherein the temporary facility is used while the existing facility is upgraded and/or remodeled.

6. The method of claim 5 wherein the existing facility is upgraded to a radiotherapy device substantially similar to the radiotherapy device in the temporary facility such that use of the radiotherapy device in the temporary facility can serve as training for the use of the upgraded device.

7. The method of claim 1 wherein the foundation comprises a pattern of reinforced concrete beams recessed below grade.

8. The method of claim 1 wherein the temporary facility is constructed on a plurality of supports extending from the foundation and terminating in an above ground mounting plate.

9. The method of claim 1 wherein the vault includes a treatment room having side walls and wherein the weight of radiation shielding material above the treatment room is born by shear walls that are outside the treatment room and spaced from the side walls.

10. The method of claim 9 wherein each shear wall is positioned over a reinforced concrete grade beam.

11. A method for providing radiotherapy while an existing radiotherapy device is taken out of service, the method comprising:
providing a radiotherapy facility having an existing radiotherapy device needing to be taken out of service;
providing a site for a temporary radiotherapy facility to be used while the existing radiotherapy device is taken out of service;
providing a foundation for the temporary radiotherapy facility at the site;
constructing a temporary radiotherapy facility on the foundation, the temporary radiotherapy facility including a radiotherapy device within a radiation shielding vault, the radiation shielding vault including at least about 1,000,000 lbs of radiation shielding material; and
removing the temporary radiotherapy facility from the site less than 12 months from the time the existing equipment is taken out of service, wherein removing the temporary radiotherapy facility includes removing the radiotherapy device and the radiation shielding vault from the site;
wherein the temporary facility is constructed on a plurality of supports extending from the foundation and terminating in an above ground mounting plate;
wherein the supports have a base plate and the base plate of the supports is provided in recesses in the foundation.

12. The method of claim 11 wherein the base plate of the supports is provided in elongated slots formed in the foundation.

* * * * *